US007866465B2

(12) United States Patent
Dverin

(10) Patent No.: US 7,866,465 B2
(45) Date of Patent: Jan. 11, 2011

(54) MULTI-COMPARTMENT STORAGE AND MIXING VESSEL

(76) Inventor: Alexander Dverin, 16 Habaal Shem Tov Street, Herzelia (IL) 46342

( * ) Notice: Subject to any disclaimer, the term of this patent is extended or adjusted under 35 U.S.C. 154(b) by 287 days.

(21) Appl. No.: 12/088,237

(22) PCT Filed: Sep. 11, 2006

(86) PCT No.: PCT/IL2006/001057

§ 371 (c)(1), (2), (4) Date: Mar. 27, 2008

(87) PCT Pub. No.: WO2007/036928

PCT Pub. Date: Apr. 5, 2007

(65) Prior Publication Data

US 2009/0014449 A1 Jan. 15, 2009

(30) Foreign Application Priority Data

Sep. 27, 2005 (IL) ..................................... 171141

(51) Int. Cl.

| | |
|---|---|
| ***B65D 25/08*** | (2006.01) |
| ***B67D 7/74*** | (2010.01) |
| ***B01F 13/00*** | (2006.01) |
| ***A61M 37/00*** | (2006.01) |

(52) U.S. Cl. .................... 206/219; 222/136; 222/145.1; 366/130; 604/89

(58) Field of Classification Search ......... 206/219–222; 222/129–145.6; 366/130–139; 604/89
See application file for complete search history.

(56) References Cited

U.S. PATENT DOCUMENTS

| | | | | |
|---|---|---|---|---|
| 3,016,896 | A * | 1/1962 | Van Sickle | 604/89 |
| 3,475,010 | A * | 10/1969 | Moline et al. | 222/136 |
| 3,477,431 | A * | 11/1969 | Walecka | 604/89 |
| 3,828,980 | A * | 8/1974 | Creighton et al. | 222/137 |
| 3,870,147 | A | 3/1975 | Orth | |
| 3,881,484 | A * | 5/1975 | Gidcumb, Jr. | 604/89 |
| 4,272,199 | A | 6/1981 | Hade | |
| 4,371,094 | A * | 2/1983 | Hutter, III | 222/136 |
| 5,215,225 | A | 6/1993 | Kopp | |
| 5,529,216 | A | 6/1996 | Klima et al. | |
| 5,702,182 | A * | 12/1997 | Alvarado | 366/130 |
| 5,954,236 | A | 9/1999 | Virnelson | |
| 6,021,892 | A | 2/2000 | Baudin | |
| 6,488,651 | B1 * | 12/2002 | Morris et al. | 604/89 |
| 6,743,194 | B2 * | 6/2004 | Sharon et al. | 604/89 |

OTHER PUBLICATIONS

International Search Report and Written Opinion dated Sep. 13, 2007, for Application No. PCT/IL2006/001057.

* cited by examiner

*Primary Examiner*—Bryon P Gehman

(57) ABSTRACT

A multi-compartment storage and mixing container for separately storing two or more components and for mixing the components in the container immediately before use. The container comprises an outer container and an inner assembly. The inner assembly comprises a plunger assembly comprising a stem and a plurality of spaced apart partitions mounted perpendicularly thereon. The inner assembly is transformable from a first storage position, where two or more separated sealed compartments are defined within the container, to a second mixing position, where there is free communication between all portions within the container.

11 Claims, 5 Drawing Sheets

MULTI-COMPARTMENT STORAGE AND MIXING VESSEL

BACKGROUND OF THE INVENTION

1. Field of the Invention

The present invention relates to containers in general and to a multi-compartment storage and mixing container, in particular.

2. Discussion of the Related Art

There exist many multiple-component solutions that become unstable once their ingredients are mixed together and therefore need to be consumed shortly after mixing. For example, it is known to prepare cocktail drinks or other multiple-component beverages immediately before serving. Although each of the cocktail ingredients may be preserved for a prolong time when kept in a separate container, once the ingredients are mixed, oxidation or other deterioration process starts. Numerous other examples of unstable multiple-components mixtures can be found in the food, chemical, cosmetic and pharmaceutical industries, e.g. hair dyes and medical prescriptions, to name only a few. Although in some cases it is possible to add preservatives and/or stabilizers in order to prolong the mixture shelf life, there are many cases where no suitable preservatives are found. Moreover, especially in the food industry, the addition of preservatives is undesired.

In such cases where it is necessary to postpone the mixing process to immediately prior to consumption, separate storage is required for each of the mixture component (or at least for those components which are unstable when mixed together). The use of a separate container for each of the ingredients is very often inconvenient and cumbersome as it requires purchasing and manipulating separate containers, measuring the necessary amounts and preparing the mixture in yet additional container. Furthermore, many times it forces a user, who wishes to prepare only a one dose amount, to purchase much larger amounts than necessary since many ingredients cannot be purchase in small amounts.

Accordingly, it is the object of the present invention to provide a container that allows for separately storing measured amounts of a mixture's ingredients and for mixing the components at the same container at the time of use for the preparation of one-dose cocktail mixes, medicinal preparations and the like.

It is another object of the invention to provide such a container which may be designed to separately contain any desired number of components and that allows f(or mixing the components when required by a simple operation.

A further object of the invention is to provide such as container which is cost effective and can be filled and assembled in series mass production.

Other advantages and benefits of the invention will be apparent from the description that follows.

SUMMARY OF THE PRESENT INVENTION

The present invention provides a multi-compartment storage and mixing container that allows for separately storing two or more components and for mixing the components in the same container when desired by the user. The container comprises an outer container and an inner assembly adapted to be housed within the outer container wherein the inner assembly is transformable from a first storage position, where two or more separated sealed compartments are defined within said container volume, to a second mixing position, where there is free communication between all portions within the container volume. The outer container is having walls and a bottom defining the container volume and a mouth for providing an access to the container volume. The inner assembly comprises a plunger assembly comprising a stem and two or more spaced apart partitions mounted thereon. The multi-compartment container further comprises a closing means for closing the outer container mouth and with at least two sealable inlet openings adapted for filling the two or more separated compartments.

In accordance with one preferred embodiment of the invention, the outer container is conically shaped and the two or more partitions are of decreasing diameter from bottom to top to fit the sloping walls of the outer container wherein the bottommost partition is having a diameter smaller than the diameter of the outer container bottom. In accordance with this embodiment, in the storage position, the plunger assembly is positioned above the container bottom pressed against the outer container walls so as to define two or more separate compartments between the partitions and the walls. In this storage position, the bottom most compartment defined between the container bottom and the bottommost partition is substantially empty. In the second mixing position the plunger assembly is shifted downwardly from the storage position to form free passages between the partitions and the container walls. Further in accordance with this embodiment, the sealable inlets for introducing substance into the separated compartments in the storage position, may be located at the outer container walls. Alternatively the sealable inlets may be two or more tubes extending from the bottommost partition of the plunger assembly and terminating each at a different compartment. Preferably, the bottom of the outer container is removable for facilitating opening and closing the bottom end of the container. The container may be further provided with a moving mechanism for moving the plunger assembly from the first storage position to the second mixing position and with a retaining mechanism for retaining the plunger assembly in the second mixing position once the plunger assembly is shifted into said second position.

In accordance with a second preferred embodiment the inner assembly is a syringe-like member further comprising a hollow member adapted to be inserted through the mouth of the outer container. According to this embodiment the inner assembly is assembled and filled prior to insertion into the outer container. In the first storage position the plunger assembly is accommodated within the hollow member so that the two or more partitions form a seal contact with the hollow member to define at least one compartment within said hollow member. An additional compartment is defined between the hollow member and the outer container walls which may be filled after the inner assembly is housed within the outer container and the plunger assembly is affixed to the outer container bottom. In the second mixing position the hollow member is removed from the outer container through the outer container mouth. The hollow member is provided with an opening configured to allow communication between inner volume of the hollow member and ambient atmosphere. Preferably, the hollow member is having an extension protruding above the outer container mouth for facilitating removal of the hollow member.

BRIEF DESCRIPTION OF THE DRAWINGS

The present invention will be understood and appreciated more fully from the following detailed description taken in conjunction with the drawings in which.

DETAILED DESCRIPTION OF THE PREFERRED EMBODIMENTS

The present invention provides a multi-compartment vessel for storing and mixing at least two components. The vessel allows for keeping the components separated from each other until consumption and for instantly mixing the components by a simple one step operation prior to consumption. The invention allows for mixing the components in the same container at which they were stored thus eliminating the need for pouring or otherwise transferring the components into another container. Moreover, storage and mixing are obtained substantially at the same volume, with only a small extra free space for allowing better mixing, so that the container volume can be kept to be substantially almost the same as the cumulative volume of the separate components. The vessel can be configured to comprise any desired number of chambers in order to accommodate separately any desired numbers of components. The components stored in the container may be liquids, dry substances or a combination thereof. The container allows for a thorough mixing of the components by providing relatively wide passage communications between the compartments once the container is turned into the mixing position. Furthermore, the containers of the invention are designed such as to allow free communication with ambient air when necessary so that no resistance develops that hinders free passage of substances from one compartment to another. Preferably, the container is pre-filled with measured amounts of the various components required for the preparation of a one-dose. For example, a container designed for a cocktail drink will contain components in amounts and ratios for one typical serving of the particular cocktail. However, it will be realized that the container of the invention may be dimensioned to contain more than one-dose or one-serving amount. For example, a container of the invention may contain measured amounts for the preparation of two typical drinks suitable to be consumed by two persons or may even assume a conventional 750 ml or 1000 ml volume of a regular drink bottle ready to be consumed by a group of people, thus saving the necessity to keep a stock of different containers for each of cocktail components or for the knowledge of the cocktail recipe. The containers of the invention may be easily fabricated from any material chemically compatible with the components to be stored therein, including plastics such as PET, glass and metal alloys. The container may be made of a transparent or opaque material if the components to be stored therein are light-sensitive. The containers the invention may be filled with measured amounts of the various components at the time of manufacturing of the container by automatic processing. Alternatively, empty containers may be provided to be filled by the user in accordance with needs.

Figures 1, 2, 3:
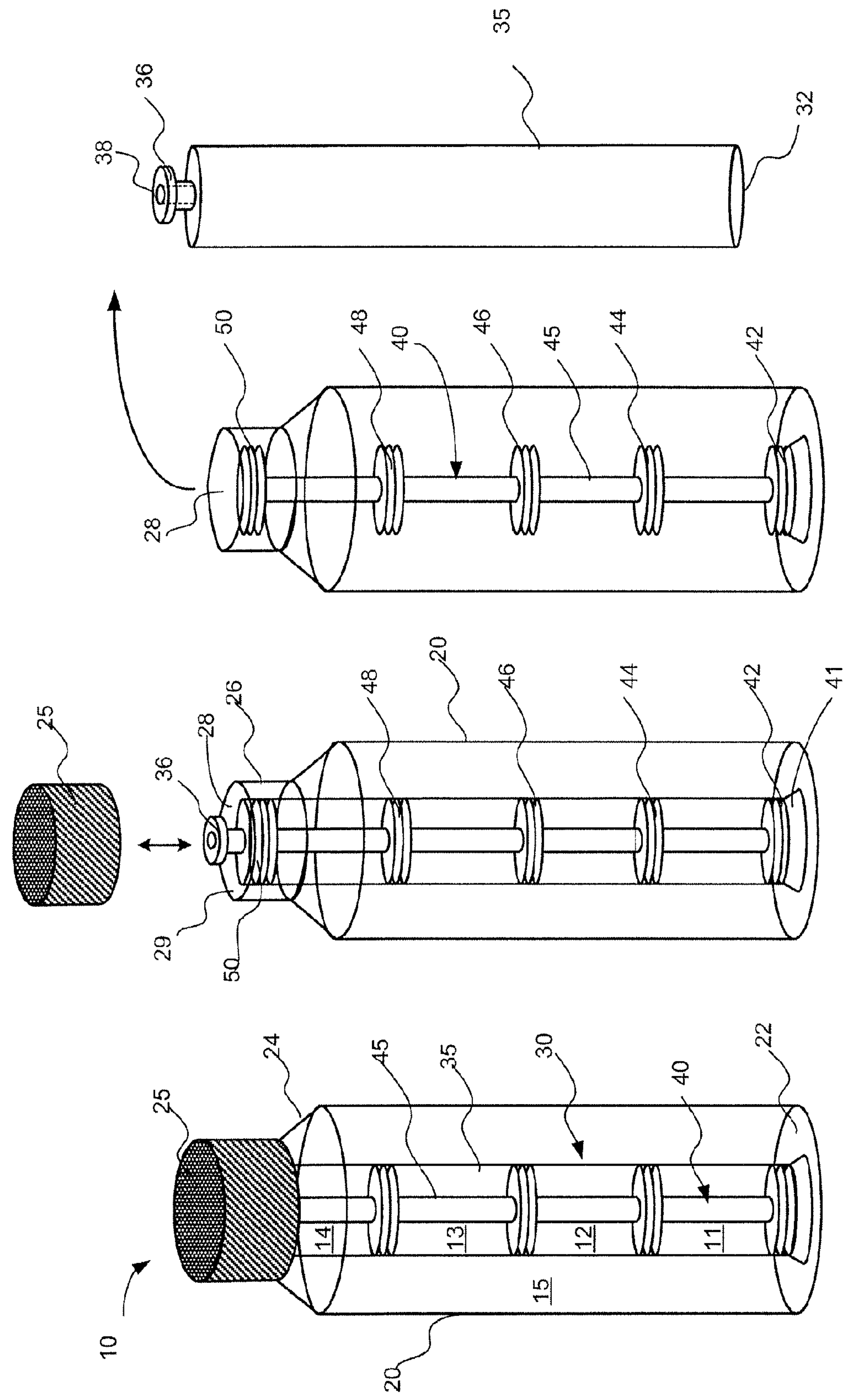
FIG. 1 is an illustration of a multi-compartment vessel of the invention showing the vessel in a storing, premixing position.
FIG. 2 is an illustration of the vessel of FIG. 1 with cap removed.
FIG. 3 is an illustration of the vessel of FIG. 1 in a mixing position.

Turning to the drawings, FIGS. 1-3 illustrate a container, generally designated 10, in accordance with a first embodiment of the invention. Container 10 comprises an outer container 20 and an internal upside-down syringe-like member 30 housed within container 20. Outer container 20, as illustrated here, is a typical cylindrical bottle having a bottom 22, a shoulder section 24, a neck section 26, a mouth opening 28 defined by lip 29 and a cap 25. Cap 25, adapted to close mouth 28 may be of any known type fitted to close a container mouth, such as a threaded cap provided with inner thread compatible with complementary outer thread provided on neck 26 (not shown), a flange cap, a snap cap or any other cap suitable for tightly seal a container mouth. It will be realized that outer vessel 20 may be any conventional available bottle and may assume any shape. For example vessel 20 need not have cylindrical walls but may have sloping walls, angular walls and may include various ornamental and decorative elements to enhance the vessel appearance.

Syringe-like member 30 comprises a hollow opened cylinder 35 terminating at one end with an open tip 36 and a plunger assembly 40 comprising a stem 45 provided with a rear partition 42, a frontal partition 50 and a plurality of partitions 44, 46 and 48 spaced therebetween. Partitions 42-50, perpendicularly mounted on stem 45, are dimensioned so as to create a seal contact with the internal surface of cylinder 35. Member 30 extends from bottom 22 of container 20 and through neck 26. Preferably, tip 36 protrudes to a small extent above lip 29 so as not to prevent cap 25 from being tightened around neck 26 but to allow convenient gripping of the tip in order to pull cylinder 35 out of the container. The outer diameter of member 30 is less than the inner diameter of neck 26 so as to leave annular opening between neck 26 and cylinder 35 for providing accessibility to compartment 15 defined between outer container 20 and inner member 30 to allow filling compartment 5 after member 30 is already assembled into container 20 (see FIG. 5VI). Tip 36 is having a tubular passage 38 opened to the internal volume of cylinder 35 to allow flow communication between the inner volume of cylinder 35 and ambient atmosphere.

FIG. 1 illustrates container 10 in a storage position. In this position, stem 45 is fully inserted into cylindrical barrel 35 such that partitions 42-50 create a seal contact with the internal surface of cylinder 35 to define four separate sealed chambers 11, 12, 13 and 14. Partitions 42-50 block communication between adjacent compartments to keep each component in a separate compartment. FIG. 3 depicts container 10 in the mixing position. In order to mix the components, cylinder 35 is pulled out of container 20 by gripping tip 36. Thus in one simple operation the borders between compartments are removed and a mixture of all the components is obtained. If desired, cap 25 can be tightened back to neck 26 after the removal of cylinder 35 and the closed container can be shaken to obtain a more thorough mixing. It will be appreciated that opening 38 at tip 36 allows for the introduction of air into cylinder 35 such that no vacuum resistance is formed inside cylinder 35 when the cylinder is pulled up, thus the cylinder can be easily and smoothly pulled out. It will be also appreciated that the specific tip design demonstrated here, which allows for both introducing of air and for convenient gripping of cylinder 35, is only a non-limiting example and that other possible designs are possible which will function to achieve the same results. For example, cylinder 35 might terminate with a flat upper surface having one or more openings to allow passage of air in and out of the cylinder and an extending handle protruding therefrom for allowing gripping and pulling the cylinder.

Container 10 and member 30 may be made of any chemical resistant material such as of glass, plastics or a combination thereof. For example cylinder 30 and plunger assembly 40 may be fabricated from plastic material while outer container 20 may be a glass bottle.

Figure 4:
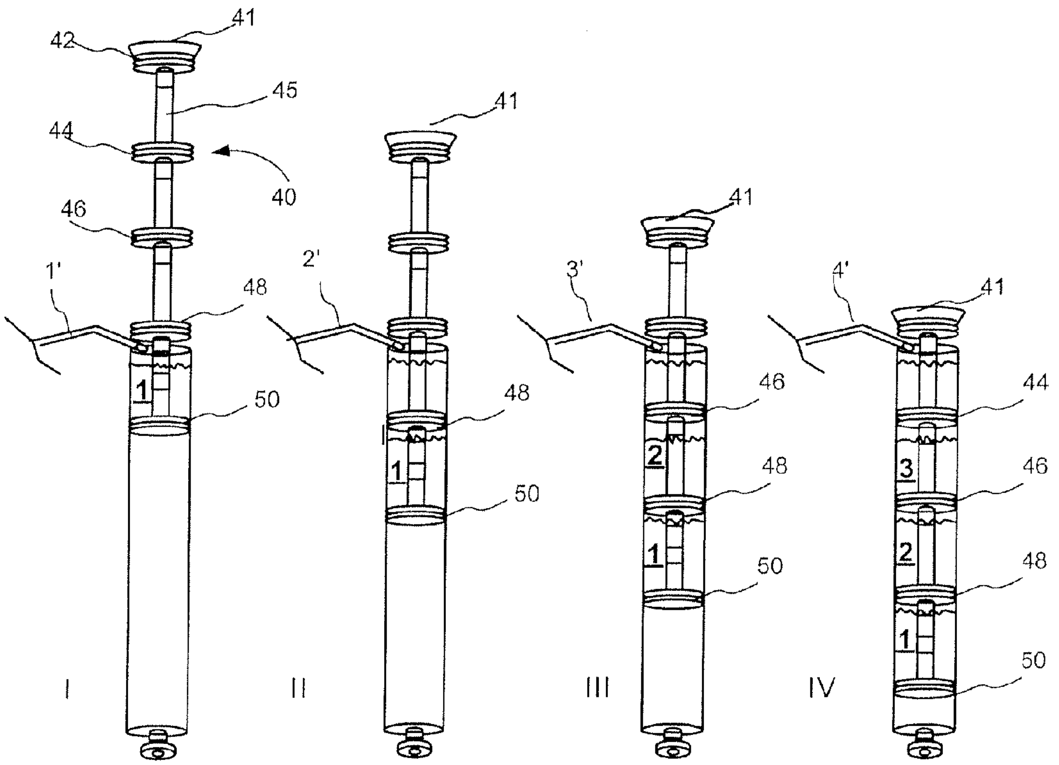
FIG. 4 is a series of illustrations I to IV demonstrating in a pictorial manner one method for filling the syringe-like member of the container of FIG. 1.
Figure 5:
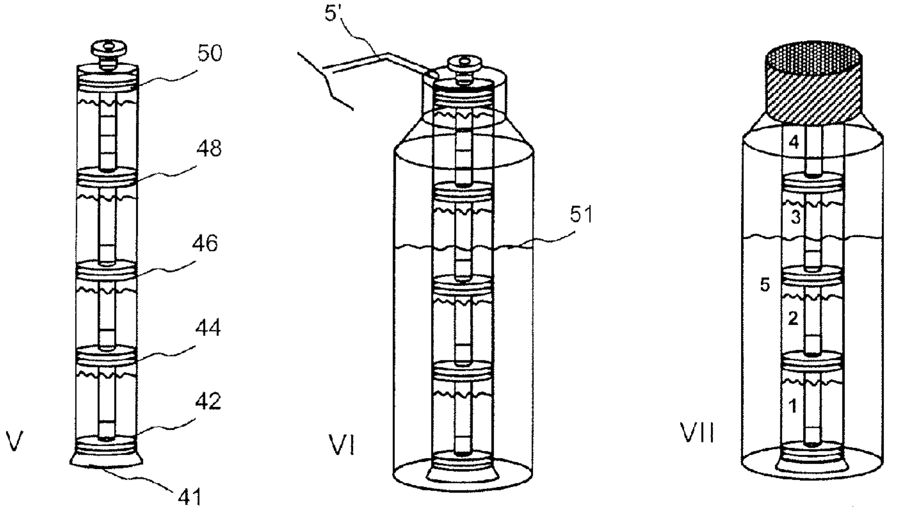
FIG. 5 is a series of illustrations V to VII demonstrating in a pictorial manner the assembling of the container of FIG. 1.

FIGS. 4 and 5 demonstrate one way for filling container 10. Referring to steps I-IV of FIG. 4, cylinder 35 is held with opening 32 directed upwardly while tip 36 is directed downwardly. Plunger assembly 40 is then inserted through opening 32 into cylinder 35 to be first stopped when partition 48 reaches a predetermined distance above opening 32. A first component 1 can then be poured through opening 32 by means of pipe 1' into first chamber 11. Rod 45 is then pushed further down to seal chamber 11 by partition 48 and until the next partition 46 approaches opening 32. A second component 2 is then poured into chamber 12 by means pipe 2' and the process repeats itself until all chambers are sealed and filled with measured amounts of components 1-4. It will be appreciated that the four pipes 1', 2', 3' and 4' may be arranged in space around opening 32 so as to enter opening 32 from different directions. It will be further appreciated that pipes 1'-4', may be each connected to a source of the corresponding component by means of a pump controlled by a controller responsible for switching the pumps on an off according to the predetermined amount of each component and to manipulate plunger assembly 40 accordingly.

Referring to FIG. 5, after member 30 is properly filled with all required components, member 30 is inverted and inserted into vessel 20 with tip 36 directed upwardly. Stopper 41 of rear partition 42 is then fixedly secured to bottom 22 of vessel 20 and held in place by attaching means such as an adhesive, glue and the like. Alternatively, member 30 may be attached to bottom 22 by mechanical means. For example, member 30 may be affixed to bottom 22 by screws inserted through the outer surface of bottom 22 and into stopper 41. Yet according to another embodiment, the inner surface of bottom 22 and the bottom face of stopper 41 may be provided with complementary mechanical means, such as inner and outer threading or complementary protrusion/recess for allowing screwing or snap-fitting member 30 onto bottom 22. An additional component 5 may then be poured into compartment 15 defined between the external surface of cylinder 35 and internal surface of vessel 20 up to a predetermined level 51 as shown in step VI. The container is then closed by cap 25 to maintain the five components in separate compartments until use. It will be appreciated that the complete assembling of container 10 including the filling process, as mentioned above, may be performed in an automatic mass production controlled process.

It will be realized that at least one of compartments 1-5 may contain dry substance in the form of powder, for example a sweetener or any other additive dissolvable in a liquid component contained in another compartment.

Figure 6:
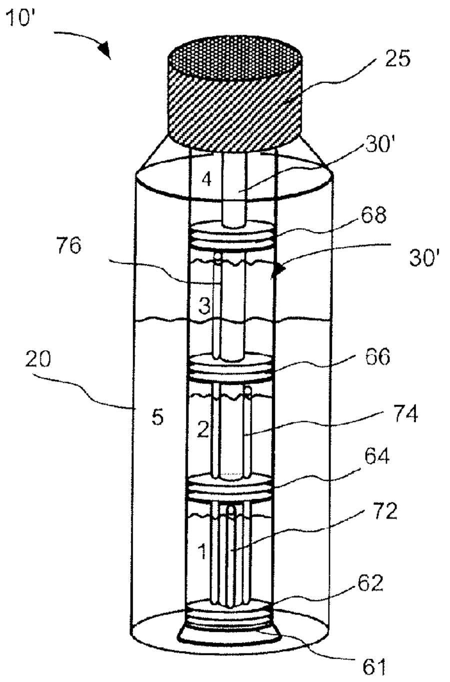
FIG. 6 depicts a multiple-compartment vessel similar to the vessel of FIG. 1 with a modified syringe-like internal member.
Figure 9:
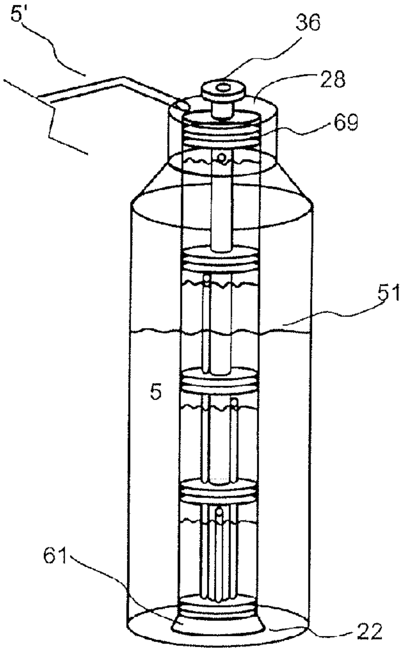
FIG. 9 illustrates the last filling step of the vessel of FIG. 6 after the internal syringe-like member is already assembled.
Figure 7:
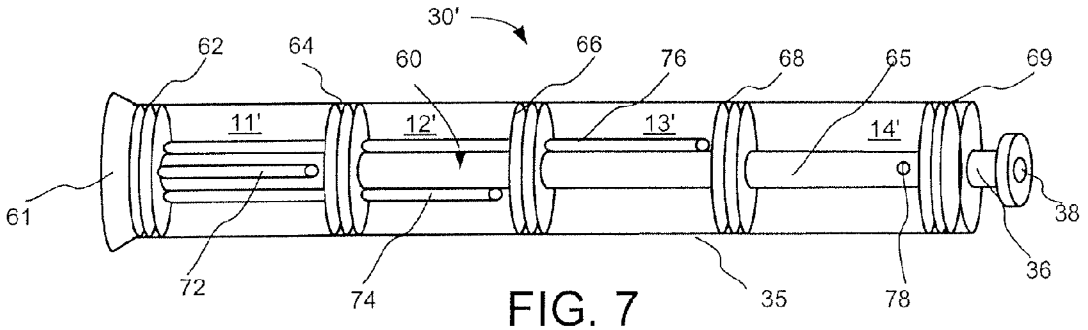
FIG. 7 is depicts the internal syringe-like member of the vessel of FIG. 6.
Figure 8:
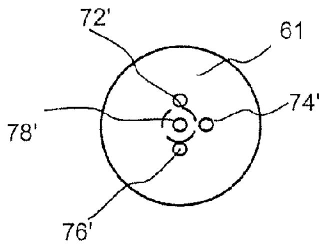
FIG. 8 is an end view of the syringe-like member of FIG. 7.

FIGS. 6 to 8 illustrate an alternative embodiment of a container, generally referred to as 10', having a modified syringe-like member 30' which provides a different way for filling the container. Similarly to container 10 described above, container 10' comprises an outer container 20 provided with cap 25 adapted to close the mouth thereof and an inner syringe-like member 30'. In accordance with embodiment 10', member 30' (shown in detail in FIG. 7) comprises an open cylinder 35 similar in shape to cylinder 35 of embodiment 10 and a plunger assembly 60 comprising a central stem 65, a plurality of partitions 62, 64, 66, 68 and 69 and a plurality of open ended tubes 72, 74 and 76 extending along stem 65. Tubes 72, 74 and 76, having inlet openings 72', 74' and 76', respectively, in stopper 61 (best seen in FIG. 8), extend to different lengths to terminate between partitions 62, 64, 66 and 68, respectively. An additional inner passage 78 having an inlet opening 78' runs through stem 65 and opens between partitions 68 and 69. Thus, in accordance with this embodiment, measured amounts of specific components can be introduced into compartments 11', 12', 13 and 14' through inlets 72', 74', 76' and 78, respectively. After filling member 30' is complete, inlet orifices 72'-78' are sealed. One way to seal the openings may be by spreading an adhesive resin on the outer surface of stopper 41 wherein small amounts of the resin will enter the inlet ends of the tubes and block the inlets. This way the resin may serve to seal the openings as well as to attach member 30' onto bottom 22 as described above. Alternatively, the openings may be sealed by small plugs or stoppers (not shown) to seal the tubes. The plugs may be small resilient tubular pieces, made out of synthetic rubber and the like, inserted into the openings to create a sealing contact with the walls of tubes 72, 74, 76 and 78. The filled syringe-like member 30' is then inverted and inserted into container 20 with stopper 61 facing downwardly to be attached to bottom 22 of vessel 20, as described above in association with FIG. 5. After member 30' is fixedly attached to bottom 22, an additional component 5 may then be poured through mouth 28 into vessel 20 to fill the space between cylinder 30 and vessel 20 up to desired level 51. Cap 25 is then secured to vessel 20 to close mouth 28 to maintain container 10' in a storage position. It will be appreciated that, as in embodiment 10, the process of filling and assembling container 10', may be an automated process. It will also be appreciated that the embodiments described in association with FIGS. 1-9 may be implemented with any available bottle providing the internal syringe-like member 30 is dimensioned so as to be of a diameter smaller than the narrowest cross section of the outer vessel and that barrel 35 is provided with means for being pulled out through the vessel mouth. Thus, there is no need for a specially designed production line for the production of container 20.

Turning now to FIGS. 10 to 13, there is illustrated another embodiment of a multi-compartment container, generally designated 100. Container 100 comprises a conically hollow outer container body 110 and an inner plunger assembly 130. Body 110 is having an open bottom end 119, a neck 118 and a mouth 128. The container further comprises a bottom cover 115 adapted to close open bottom 119 after plunger assembly 130 is placed inside body 110 and a cap 125 adapted to be mounted on threaded neck 118 for closing mouth 128. Plunger assembly 130 includes a central rod 140 and a plurality of spaced apart partitions 141-146 of decreasing diameter dimensioned to fit the inner perimeter of the sloped walls of body 110. The conically-shaped sloping wall of vessel 110 is interrupted by small vertical sections 121-126 for facilitating seal contact between partitions 141-146 and wall. A plurality of inlet openings 151, 152, 153, 154 and 155, located between successive vertical sections 121-126, are provided in the walls of body 110. FIGS. 10A and 10B show container 100 in a storage position and in a mixing position, respectively. In the storage position, plunger assembly 130 is placed such that lower partition 141 is pressed against vertical annular section 121 while successive partitions 142 to 146 of decreasing diameter are pressed against sections 122 to 126, respectively, to define compartments 111-115 and 118. In the storage position, the lowest compartment 118 is left empty or optionally is filled with a small amount of solid substance such as to leave most of the compartment volume free. Filling compartments 111 to 115 is performed through openings 151 to 155 wherein each compartment is filled with a measured amount of a different component. After filling is complete, openings 151-155 are sealed. One way to seal openings 151-155 may be by a food compatible resin. In accordance with one embodiment, the resin may be spread around each of the openings to form a seal of a defined shape, which may be stamped by a certain stamp before the resin hardens. This way, the authenticity of the container content may be validated. Alternatively, openings 151-155 may be sealed by means of small resilient plugs.

Figure 10A:
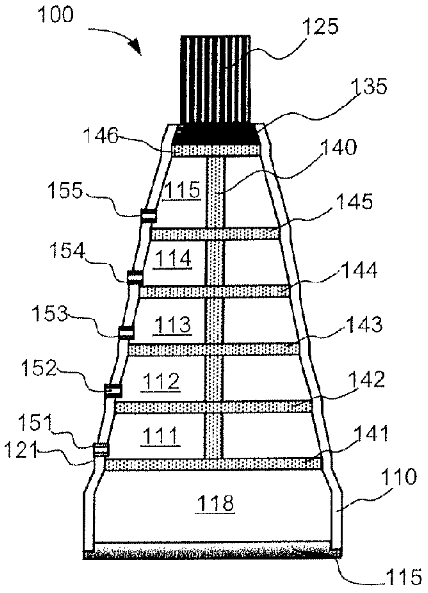
FIGS. 10A and 10B depict a vessel in accordance with yet another embodiment of the invention showing the vessel in a storage position and in a mixing position, respectively.
Figure 10B:
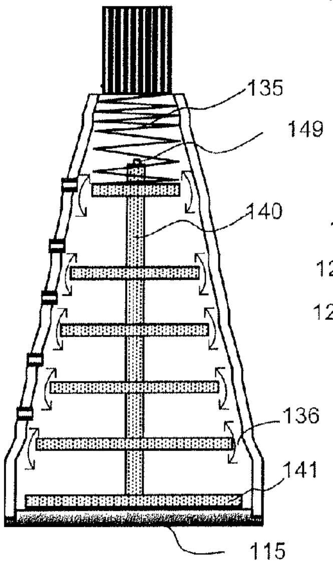
Figure 11:
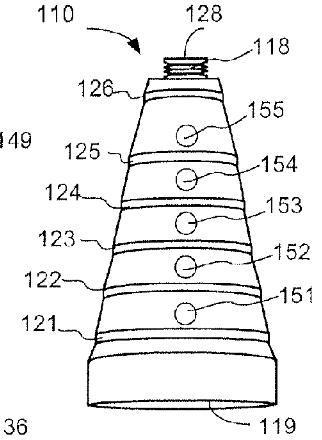
FIG. 11 shows the outer component of the vessel of FIG. 10.
Figure 12:
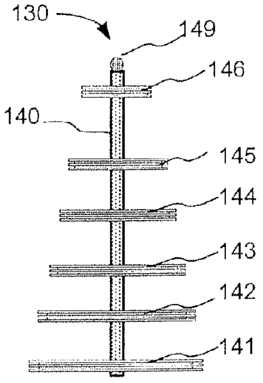
FIG. 12 shows the internal element of the vessel of FIG. 10.
Figure 13A:
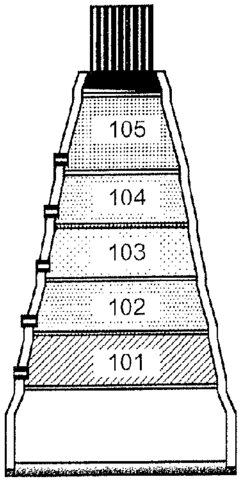
FIGS. 13A and 13B illustrate the vessel of FIG. 10 in a filled storage position and in a mixing position, respectively.
Figure 13B:
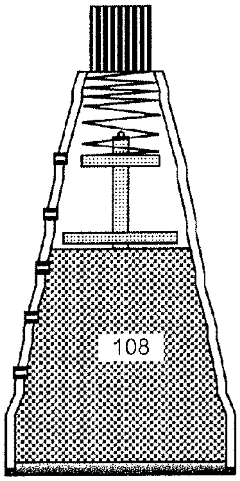

In order to mix the components, plunger 130 is pushed downwardly toward bottom 115 such that each of partitions 141-146 is now located against a section of container 110 having a larger diameter than the partition diameter, as is shown in FIG. 10B. At this position the compartments are not separated any more and the components come into contact with each other through passages 136 between partitions and wall as indicated by the arrows in FIG. 10B. FIG. 13A illustrates container 100 in the storage position having compartments 111 to 115 filled with different components 101 to 105, respectively. FIG. 13B illustrates the container after plunger assembly 130 has been moved to the mixing poison to obtain mixture 108. It will be appreciated that since compartment 118 is substantially empty, pushing assembly plunger 130 downwardly against the air in compartment 118 does not encounter much resistance. In accordance with the embodiment shown here, container 100 is provided with a helical compression spring 135 for facilitation pushing down rod 140 into the mixing position without opening the container. In the storage pre-mixing position, spring 135, having a diameter of substantially the inner upper most diameter of body 110, is compressed between upper partition 146 and the upper wall 117 of container 110. Upon rotation of cap 125 relative to neck 118, spring 135 is released to push down plunger assembly 130 into the mixing position and to maintain the plunger in this position. The container may then be shaken to thoroughly mixing the components while cap 125 is on. It will be appreciated that the spring release mechanism described herein is given by a way of non-limiting example only and that other possible ways may be employed to facilitate moving plunger assembly 130 into the mixing position without departing from the scope of the invention. For example, plunger assembly 130 may be simply pushed down manually by pressing down end 149 of rod 140. A one-direction movement mechanism may farther be provided for preventing reverse movement of rod 140 in the upward direction and for retaining the plunger assembly 130 in the mixing position. A non-limiting example for such a mechanism may be angled teeth provided on the upper portion of rod 140 and a ring suspended at the container's mouth that encircles the rod and is configured so as to allow movement in the downward direction only. However, it will be realized that many other mechanisms are possible for retaining and/or locking plunger assembly 130 in the mixing position once it is moved into this position, without departing from the scope of the invention.

Figure 14A:
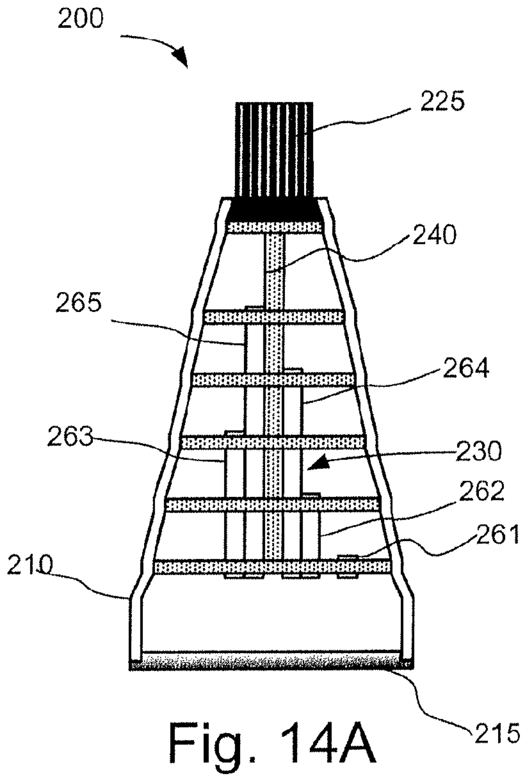
FIGS. 14A and 14B illustrate a modified embodiment of a vessel similar to the vessel of FIG. 10.
Figure 14B:
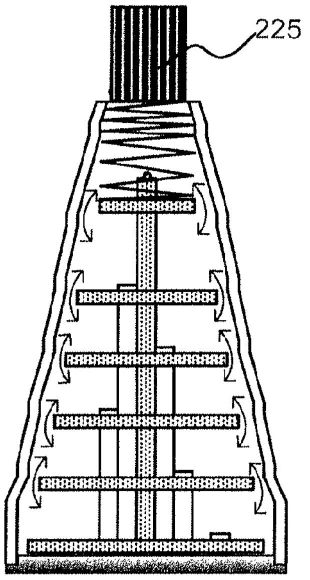
Figure 15:
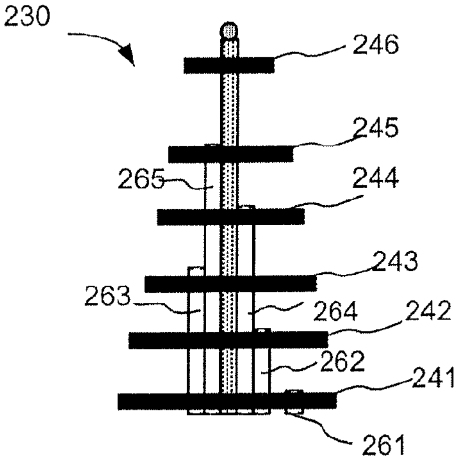
FIG. 15 depicts the internal member of the vessel of FIG. 14.
Figure 16:
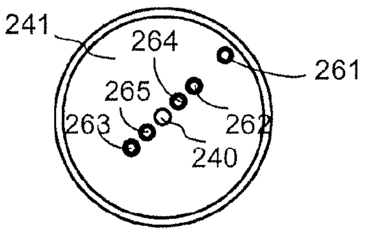
FIG. 16 is a bottom plan view of the internal element of FIG. 15.

FIGS. 13 to 15 depict a modified embodiment, generally designated 200, of the container of FIG. 10, according to which instead of openings in the wall of container 110, the plunger assembly is provided with a plurality of tubes for facilitating filling the separate compartments. Container 200 comprises a hollow conically shaped container body 210 similar in shape to body 110 described above, and a plunger assembly 230. A bottom cover 215 is adapted to close the wider bottom open end of body 210 and a cap 225 is configured to be mounted on the neck of vessel 210 for closing the mouth thereof. In accordance with this embodiment, plunger assembly 230 comprises, in addition to stem 240 and partitions 241 to 246, a plurality of tubes 261 to 265 extending from widest partition 241 and terminating in compartments 211-215, respectively. According to this embodiment container 200 is filled with measured amounts of the different components through tubes 26 while being held upside down. Stoppers (not shown) are then inserted into the openings to seal the compartments and bottom cover 215 is attached to body 210.

It will be appreciated that the multi-compartment containers of the invention may be easily designed to include any number of separate compartments in accordance with the mixture to be stored therein. However, it will be also appreciated that the number of compartments does not necessarily have to be equal to the number of ingredients in the mixture. For example, depending on the specific mixture and the ratio between its ingredients, a container of a certain number of compartments may contain a lesser number of ingredients wherein several compartments may be filled with the same ingredient or may be left empty, or may contain a larger number of ingredients wherein two or more chemically compatible ingredients may be stored in the same compartment. Further, it will be realized that the containers of the invention allow for preparing the mixture in the same container in which the mixture components have been separately stored. However, this does not imply that the mixture need not be consumed from the container. Rather, after mixing, the mixture can easily be transferred into another vessel to be consumed therefrom.

It will be appreciated by persons skilled in the art that the present invention is not limited to what has been particularly shown and described hereinabove. Rather the scope of the present invention is defined only by the claims which follow.

The invention claimed is:

1. A multi-compartment storage and mixing container for separately storing two or more components and for mixing the components in said container before consumption, the container comprising:

an outer container having walls, a bottom and a mouth; and an inner assembly adapted to be housed within said outer container, the inner assembly comprising a hollow elongated unit and a plunger assembly adapted to fit into said hollow elongated unit, the plunger assembly comprising a stem and two or more spaced apart partitions fixedly mounted thereon;

wherein said inner assembly is transformable from a storage position, where two or more separated compartments are defined within said outer container, to a mixing position, where there is a free communication between all portions within said outer container; and wherein in the storage position the plunger assembly is accommodated within said hollow elongated unit so that the two or more partitions form a seal contact with the hollow elongated unit to define at least one compartment within said hollow elongated unit and an additional compartment between the hollow elongated unit and the outer container's walls and wherein in the second mixing position said hollow member is removed from said outer container through said mouth.

2. The multi-compartment storage and mixing container of claim 1 wherein at least one of said two or more components is a liquid.

3. The multi-compartment storage and mixing container of claim 1 wherein at least one of said two or more components is a solid.

4. The multi-compartment storage and mixing container of claim 1 wherein said plunger assembly is affixed to the outer container.

5. The multi-compartment storage and mixing container of claim 1 wherein said hollow member is provided with an opening configured to allow communication between the inner assembly and ambient atmosphere.

6. A multi-compartment storage and mixing container for separately storing two or more components and for mixing the components in said container before consumption, the container comprising an outer container having walls, a bottom and a mouth, an inner assembly configured to be inserted into said outer container through said mouth, the inner assembly comprising a hollow elongated unit and a plunger assembly adapted to fit into said hollow unit, the plunger assembly comprising a stem and two or more spaced apart partitions fixedly mounted on the stem, the two or more partitions are configured to form a seal contact with said hollow unit so as to define at least one sealed compartment;

wherein said hollow unit is movable between a storage position and a mixing position and wherein said stem and two or more partitions maintain their position with respect to each other when said hollow unit is moved from the storage position to the mixing position; and wherein in the storage position the plunger assembly is fully accommodated within the hollow unit and in the mixing position the hollow unit is removed from the outer container.

7. The multi-compartment storage and mixing container of claim 6 wherein said plunger assembly is affixed to the outer container.

8. The multi-compartment storage and mixing container of claim 6 wherein said hollow unit has an extension protruding above the outer container's mouth for facilitating removal of the hollow unit.

9. The multi-compartment storage and mixing container of claim 6 wherein said hollow unit is provided with an opening configured to allow communication between the inner assembly and ambient atmosphere.

10. The multi-compartment storage and mixing container of claim 6 wherein the inner assembly is assembled and filled prior to insertion into the outer container.

11. The multi-compartment storage and mixing container of claim 10 wherein an additional compartment is defined between the inner assembly and the outer container.

* * * * *